(12) United States Patent
Zhang et al.

(10) Patent No.: US 12,327,376 B2
(45) Date of Patent: Jun. 10, 2025

(54) METHOD AND APPARATUS FOR PROCESSING SCANNING DATA, DEVICE, AND MEDIUM

(71) Applicant: Shining 3D Tech Co., Ltd., Zhejiang (CN)

(72) Inventors: Yuansong Zhang, Zhejiang (CN); Xiaojun Chen, Zhejiang (CN); Jian Zhang, Zhejiang (CN); Tengfei Jiang, Zhejiang (CN); Xiaobo Zhao, Zhejiang (CN)

(73) Assignee: SHINING 3D TECH CO., LTD., Zhejiang (CN)

( * ) Notice: Subject to any disclaimer, the term of this patent is extended or adjusted under 35 U.S.C. 154(b) by 0 days.

(21) Appl. No.: 18/925,697

(22) Filed: Oct. 24, 2024

(65) Prior Publication Data

US 2025/0054186 A1     Feb. 13, 2025

Related U.S. Application Data

(63) Continuation of application No. PCT/CN2023/091806, filed on Apr. 28, 2023.

(30) Foreign Application Priority Data

May 2, 2022   (CN) .......................... 202210494057.6

(51) Int. Cl.
G06T 7/73       (2017.01)
A61C 13/00      (2006.01)
G06T 7/33       (2017.01)

(52) U.S. Cl.
CPC ............ G06T 7/74 (2017.01); A61C 13/0004 (2013.01); G06T 7/337 (2017.01); G06T 2207/10012 (2013.01); G06T 2207/30036 (2013.01)

(58) Field of Classification Search
None
See application file for complete search history.

(56) References Cited

U.S. PATENT DOCUMENTS

2002/0006217 A1   1/2002   Rubbert
2012/0035889 A1   2/2012   Lawitschka et al.
(Continued)

FOREIGN PATENT DOCUMENTS

CN     109272454 A     1/2019
CN     109523578 A     3/2019
(Continued)

OTHER PUBLICATIONS

International Search Report dated Aug. 6, 2023 issued in PCT/CN2023/091806.
(Continued)

*Primary Examiner* — Xiaolan Xu
(74) *Attorney, Agent, or Firm* — Scully, Scott, Murphy & Presser, P.C.

(57) ABSTRACT

Embodiments of the present disclosure relate to a method and apparatus for processing scanning data, a device, and a medium. The method includes: obtaining a plurality of frames of images to be processed including auxiliary feature points, where the auxiliary feature points have corresponding distribution true values; performing processing based on the plurality of frames of images to be processed to obtain all three-dimensional coordinate points in a same coordinate system in conjunction with a current camera pose; performing measurement processing on all the three-dimensional coordinate points to obtain target three-dimensional coordinate points; and determining a target position transformation relationship based on the target three-dimensional coordinate points and the distribution true values.

16 Claims, 6 Drawing Sheets

(56) References Cited

U.S. PATENT DOCUMENTS

| | | | |
|---|---|---|---|
| 2017/0119505 A1 | 5/2017 | Werner | |
| 2020/0100881 A1* | 4/2020 | Emery, III | A61C 8/0009 |
| 2022/0369935 A1* | 11/2022 | Chang | G06T 7/149 |
| 2023/0240818 A1* | 8/2023 | Querbes | G06T 7/337 |
| | | | 433/29 |

FOREIGN PATENT DOCUMENTS

| | | |
|---|---|---|
| CN | 208552101 U | 3/2019 |
| CN | 113483695 A | 10/2021 |
| CN | 113491533 A | 10/2021 |
| CN | 215384788 U | 1/2022 |
| CN | 114343895 A | 4/2022 |
| CN | 114869528 A | 8/2022 |
| DE | 102019100220 A1 | 7/2020 |
| DE | 102019100221 A1 | 7/2020 |
| EP | 3629336 A1 | 4/2020 |

OTHER PUBLICATIONS

Chinese First Office Action dated Apr. 17, 2024 issued in CN 202210494057.6.
Notice of Reasons for Refusal dated Feb. 4, 2025 received in Japanese Patent Application No. 2024-540057.
Du, S. et al., "An Extension of the ICP Algorithm Considering Scale Factor", IEEE International Conference, 2007, pp. V-193 to V-196.
Szeliski, R: "Computer Vision:Algorithms and Applications", 2009,pp. 1-979.
Extended European search report dated Mar. 26, 2025 received in European Patent Application No. 23799238.3.

\* cited by examiner

METHOD AND APPARATUS FOR PROCESSING SCANNING DATA, DEVICE, AND MEDIUM

The present disclosure claims priority to Chinese Patent Application No. 202210494057.6, entitled "METHOD AND APPARATUS FOR PROCESSING SCANNING DATA, DEVICE, AND MEDIUM" filed with China National Intellectual Property Administration on May 2, 2022, which is incorporated herein by reference in its entirety.

TECHNICAL FIELD

The present disclosure relates to the technical field of intraoral scanning, and in particular to a method and apparatus for processing scanning data, a device, and a medium.

BACKGROUND

Typically, in a scenario of restoring missing teeth within an oral cavity, scan posts perform scanning to determine an implant position.

In the related art, due to the limitation of the scanning range of an oral scanner, a multi-data registering solution is usually used when intraoral data is scanned, ultimately resulting in not high overall accuracy of a model due to the existence of cumulative errors.

SUMMARY

Embodiments of the present disclosure provide a method and apparatus for processing scanning data, a device, and a medium, including the following:

In a first aspect, a method for processing scanning data is provided. The method includes:
- obtaining a plurality of frames of images to be processed, wherein each frame of images to be processed includes auxiliary feature points, the auxiliary feature points have corresponding distribution true values;
- performing processing based on the plurality of frames of images to be processed to obtain all three-dimensional coordinate points in a same coordinate system;
- performing measurement processing on all the three-dimensional coordinate points to obtain target three-dimensional coordinate points; and
- determining a target position transformation relationship based on the target three-dimensional coordinate points and the distribution true values.

In a second aspect, an apparatus for processing scanning data is further provided. The apparatus includes:
- an image obtaining component, configured to obtain a plurality of frames of images to be processed, wherein each frame of images to be processed includes auxiliary feature points, the auxiliary feature points have corresponding distribution true values;
- an image processing component, configured to perform processing based on the plurality of frames of images to be processed to obtain all three-dimensional coordinate points in a same coordinate system;
- a measurement processing component, configured to perform measurement processing on all the three-dimensional coordinate points to obtain target three-dimensional coordinate points; and
- a determination component, configured to determine a target position transformation relationship based on the target three-dimensional coordinate points and the distribution true values.

In a third aspect, an electronic device is further provided. The electronic device includes: a processor; a memory configured to store executable instructions of the processor. The processor is configured to read the executable instructions from the memory and execute the instructions to implement the method for processing scanning data provided by some embodiments of the present disclosure.

In a fourth aspect, a computer storage medium is further provided. The storage medium stores a computer program. The computer program is configured to execute the method for processing scanning data provided in the first aspect of the present disclosure.

It should be understood that the above general description and the following detailed description are only exemplary and explanatory, and cannot limit the present disclosure.

BRIEF DESCRIPTION OF FIGURES

Accompanying drawings herein are incorporated into the specification to form a part of the specification, illustrate embodiments conforming to the present disclosure, and are used for explaining the principle of the present disclosure together with the specification.

In order to describe technical solutions in embodiments of the present disclosure or in the prior art more clearly, the accompanying drawings required to be used in descriptions of the embodiments or the prior art will be briefly introduced below, and it is apparent that those of ordinary skill in the art can obtain other drawings according to these accompanying drawings without creative work.

DETAILED DESCRIPTION

To make objectives, technical solutions, and advantages of embodiments of the present disclosure clearer, the technical solutions in the embodiments of the present disclosure are clearly and completely described as below, and it is apparent that the described embodiments are a part rather all of embodiments of the present disclosure. Based on the embodiments of the present disclosure, all other embodiments obtained by those of ordinary skill in art without creative work shall fall within the scope of protection of the present disclosure.

During practical application, in a scenario of restoring missing teeth within an oral cavity, due to the limitation of the scanning range of an oral scanner, a multi-data registering solution is usually used when intraoral data is scanned, ultimately resulting in not high overall accuracy of a model due to the existence of cumulative errors.

Figure 1:
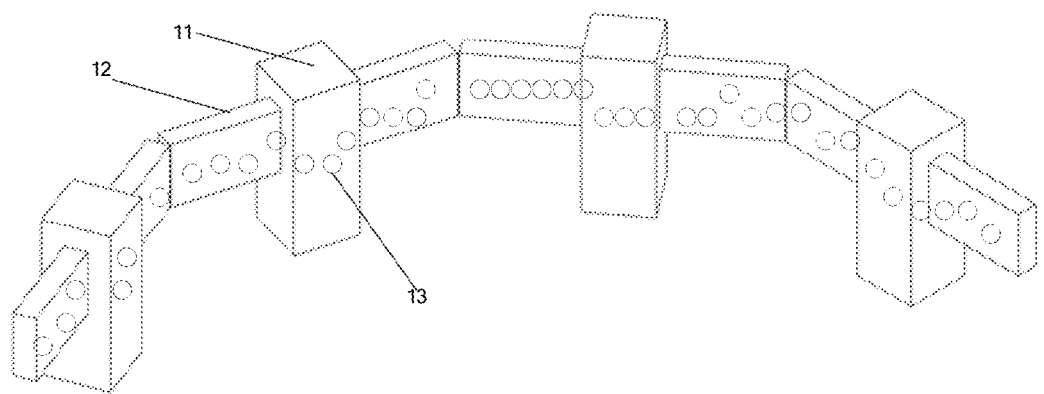
FIG. 1 is a diagram of an application scenario of processing scanning data according to an embodiment of the present disclosure.

In response to the above problems, the present disclosure provides a method for processing scanning data, which can be applied to an application environment shown in FIG. 1. FIG. 1 is a diagram of an application scenario of processing scanning data according to an embodiment of the present disclosure. The application scenario includes: installing a plurality of intraoral scan posts in a target oral cavity. Each of the intraoral scan posts includes: a scan post component 11 and an auxiliary component 12 connected with the scan post component 11. The scan post component 11 and/or the auxiliary component 12 are/is provided with auxiliary feature points, where shape features of the auxiliary component 12 are auxiliary features. The scan post component 11 is adaptive to an implant installed in the target oral cavity, and through adaptive installation of the scan post component 11 and the implant, the intraoral scan post is installed in the target oral cavity.

The auxiliary feature points may include, but are not limited to: reference points, which include: non-coded reference points and coded reference points. In some embodiments of the present application, non-coded reference points are preferred, which generally adopt circular reference points or annular reference points. In some embodiments, the target point within the reference point (generally the geometric center of the reference point, such as the center of a circle) is extracted and calculated, and the distance between two reference points is determined through the target point. Based on the distance between the reference points, matching reference point pairs in the known reference point data are determined (for example, by calculating the distance between the reference point and the reference points in the known reference point data, and determining the reference point pair with the smallest distance from the current reference point to form a reference point pair), thereby achieving reference point registering.

The auxiliary components 12 of any two of the plurality of intraoral scan posts are adaptive to each other, such that when the any two intraoral scan posts 10 are adjacently installed in the oral cavity, the auxiliary feature points on the two auxiliary components are continuously distributed. True value coordinate points of the auxiliary feature points can be obtained in advance through a single-lens reflex photogrammetry system, a coordinate measuring machine, etc. In theory, three-dimensional coordinate points corresponding to an image obtained through scanning are in one-to-one correspondence with the true value coordinate points of the auxiliary feature points obtained in advance.

The true value data of the above reference points (i.e., the true value coordinate points of the above auxiliary feature points) can be stored in a database, namely, a scanning post database. This scanning post database records multiple scanning post contours and the true value data of reference points, and the true value data of each scanning post is independent of each other and may be called separately.

As an example scenario, a plurality of intraoral scan posts is installed in the target oral cavity. The intraoral scan post includes a scan post component used for being connected with the implant, and an auxiliary component connected with the scan post component. The intraoral scan post has target features, and the target features are continuously distributed on the scan post and/or the auxiliary component, and are distributed non-unilaterally on the scan post and/or the auxiliary component.

In some embodiments, the intraoral scanner scans the target oral cavity to obtain a plurality of frames of images, and transmits the images to a data processing component for data processing. The data processing component executes the following method:

A plurality of frames of images are obtained, initial three-dimensional data of the target oral cavity is acquired based on the plurality of frames of images, and the initial three-dimensional data includes an initial point set of the target oral cavity and three-dimensional coordinate measured values of the target features in the same coordinate system.

A preset model of the intraoral scan post is obtained, and includes three-dimensional coordinate true values of the target features and a real point set (three-dimensional coordinate true values of various points) of the intraoral scan post in the same coordinate system.

The initial point set of the target oral cavity and the real point set of the intraoral scan post are registered based on a corresponding relationship between the three-dimensional coordinate measured values of the target features and the true values.

Positioning information of the intraoral scan post is determined based on the registered real point set of the intraoral scan post, the positioning information of the intraoral scan post is positioning information of the implant, and dental prosthesis design is performed based on the positioning information, such that a designed and manufactured dental prosthesis can be adaptively installed with the implant.

In some embodiments, a plurality of frames of images to be processed including auxiliary feature points are obtained, the auxiliary feature points have corresponding distribution true values, and processing is performed based on the plurality of frames of images to be processed to obtain all three-dimensional coordinate points in the same coordinate system. Measurement processing is performed on all the three-dimensional coordinate points to obtain target three-dimensional coordinate points. Based on the target three-dimensional coordinate points and the distribution true values, a target position transformation relationship is determined. Thus, the target position transformation relationship is determined based on the distribution true values preset for the auxiliary feature points and the three-dimensional coordinate points calculated through scanning, thereby accurately locating the relative position between the scan posts, and improving the data processing efficiency and accuracy in the intraoral scanning scenario.

It can be seen that the acquisition of positioning information of the scanning post can be manifested in the following process:

Obtaining the positional information of a single scanning post (including the center point and axis direction), for example, by scanning the image of each scanning post installed in the oral cavity with an intraoral scanner; identifying the reference points from the image of the scanning post, and then using the geometric center of the reference points as the position of the reference points, and thus calculating the center point and axis direction of the scanning post, thereby determining the positional information of a single scanning post;

Obtaining the relative positional information of the overall scanning posts (i.e., multiple scanning posts in the oral cavity), such as determining the relative positions of the scanning post brackets based on the reference points on the scanning posts;

Wherein the positional information of a single scanning post and the positional information of multiple scanning posts can be acquired through the registered data obtained after aligning the scanning data with the pre-stored model data, or it can be acquired through the splicing data of the preset models of multiple scanning posts. The positional information of the single scanning post and multiple scanning posts can be determined through marker point data, or through point cloud data, or determined by both together.

In the process of continuously scanning the scanning posts in the oral cavity, the scanning data (including but not limited to the reference point data of the scanning posts) is first obtained, and the reference point data of the scanning posts is spliced between frames to form a continuous image of the internal structure of the oral cavity;

During the scanning process of scanning data, it is continuously matched with the pre-stored standard data (i.e., the model data) of multiple scanning posts, and the matched standard data of the scanning posts is registered with the scanning data to achieve a unified coordinate system through the splicing of the matched standard data of multiple scanning posts with the scanning data. For example, at the very first moment of continuous scanning, the first scanning data is obtained. The first scanning data is matched with the pre-stored standard data of multiple scanning posts, and the standard data of the first scanning post that is matched is registered with the first scanning data. At the second moment of continuous scanning, the second scanning data is obtained. The second scanning data is matched with the pre-stored standard data of multiple scanning posts, and the standard data of the second scanning post that is matched is spliced with the second scanning data. The second scanning data is obtained by scanning and updating based on the first scanning data, therefore, the standard data of the first scanning post and the standard data of the second scanning post achieve a unified coordinate system.

During the scanning process, it is necessary to align and splice the scanned reference point data. At this time, the scanned reference point data is matched with the standard data of the scanning post reference points (i.e., compared and adjusted), which can reduce the splicing error. That is, the accuracy of the inter-frame splicing of the scanning post reference point data can be optimized by using the reference point data of the scanning post. In addition, since the true value data of each scanning post corresponds to a coordinate system, the data of different scanning posts can be unified into one coordinate system by using the reference point data, thereby ensuring the consistency and accuracy of the overall scanning data.

Figure 2:
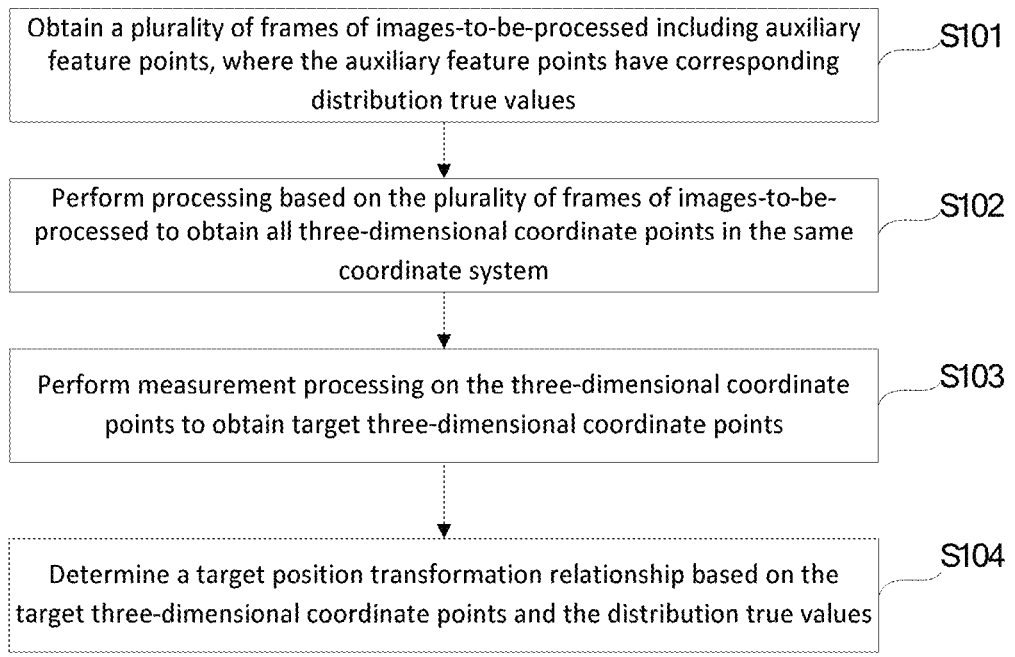
FIG. 2 is a schematic flowchart of a method for processing scanning data according to an embodiment of the present disclosure.

In some embodiments, FIG. 2 is a schematic flowchart of a method for processing scanning data according to an embodiment of the present disclosure. The method can be executed by an apparatus for processing scanning data. The apparatus may be implemented by software and/or hardware, and may be typically integrated in an electronic device. As shown in FIG. 2, the method includes the following steps:

Step 101: A plurality of frames of images to be processed including auxiliary feature points are obtained, where the auxiliary feature points have corresponding distribution true values.

A scan post includes a scan post body and an auxiliary feature body. The scan post body is provided with auxiliary feature points; alternatively, the scan post body is not provided with auxiliary feature points, and the auxiliary feature body within the scan post body is provided with auxiliary feature points; and alternatively, a shape of the auxiliary component serves as auxiliary feature points.

The target oral cavity refers to an oral cavity needing dental implanting. Intraoral scanning needs to be performed so as to locate implant points in the oral cavity. Auxiliary components of any two of a plurality of intraoral scan posts are adjacently installed in the target oral cavity in advance, and auxiliary feature points on the two auxiliary components are continuously distributed, such that intraoral scanning can be performed on the target oral cavity to obtain the plurality of frames of images to be processed.

The target oral cavity can be scanned through a handheld intraoral scanner (monocular or binocular camera). In other words, the plurality of frames of images to be processed are obtained in a photography manner, for example, dozens of frames of images to be processed are collected per second, and cyclic acquisition can be performed.

In some embodiments of the present disclosure, the scan post is a feature object including the auxiliary feature points. Each of the auxiliary feature points can uniquely identify one feature. That is, the scan post is provided with the auxiliary feature points, and each auxiliary feature point can uniquely identify a corresponding position feature on the scan post. For example, a target feature a and a target feature b are respectively set for a position 1 and a position 2 on the scan post, the target feature a can uniquely identify the position feature of the position 1 on the scan post, and the target feature b can uniquely identify the position feature of the position 2 on the scan post.

It is to be understood that different shapes, colors, two-dimensional codes, etc. on the scan post that can uniquely identify the corresponding position features on the scan post can be taken as the auxiliary feature points.

In some embodiments, the distribution true values of the auxiliary feature points or distribution true values of the auxiliary feature points obtained through computer-aided design, namely, coordinate values of the auxiliary feature points, can be obtained through a higher-precision device, such as a single-lens reflex photogrammetry system and a coordinate measuring machine.

In some embodiments of the present disclosure, the image to be processed obtained through scanning each time includes at least a preset number of auxiliary feature points to represent distribution continuity of the auxiliary feature points, thereby ensuring subsequent calculation accuracy, where the preset number may be set according to the application scenario.

For example, when the preset number is 3 and the image to be processed obtained through scanning includes 2 auxiliary feature points, it indicates that distribution of the auxiliary feature points is discontinuous, and when the image to be processed obtained through scanning includes 3 or more auxiliary feature points, it indicates that distribution of the auxiliary feature points is continuous.

In some embodiments of the present disclosure, there are various methods for obtaining a plurality of frames of images to be processed. In some implementations, a monocular camera is controlled to rotate in a specific direction while scanning the target oral cavity at a certain frequency, thereby obtaining the plurality of frames of images to be processed.

In some other implementations, a binocular camera is controlled to cyclically scan the target oral cavity to obtain the plurality of frames of images to be processed. The above two methods are only examples for obtaining a plurality of frames of images to be processed. Some embodiments of the present disclosure do not limit a specific method for obtaining a plurality of frames of images to be processed.

In some embodiments, after the target oral cavity is connected with the scan posts, the target oral cavity including the scan posts is scanned to obtain the plurality of frames of images to be processed.

Step 102: Processing is performed based on the plurality of frames of images to be processed to obtain all three-dimensional coordinate points in the same coordinate system.

All the three-dimensional coordinate points refer to three-dimensional coordinate points corresponding to all auxiliary feature points in the target oral cavity.

In some embodiments of the present disclosure, there are various methods for performing processing based on a plurality of frames of images to be processed to obtain all three-dimensional coordinate points in the same coordinate system. In some implementations, two-dimensional coordinate points of auxiliary feature points in each frame of image to be processed are obtained, three-dimensional reconstruction is performed based on a preset intrinsic matrix and the two-dimensional coordinate points to obtain three-dimensional coordinate points corresponding to the auxiliary feature points in each frame of image to be processed, and the three-dimensional coordinate points corresponding to the auxiliary feature points in the plurality of frames of images to be processed are registered to obtain the three-dimensional coordinate points for the auxiliary feature points in the plurality of frames of images to be processed in the same coordinate system.

In some other implementations, two-dimensional coordinate points of auxiliary feature points in each frame of image to be processed are obtained, three-dimensional reconstruction is performed based on a relative position between two cameras and the two-dimensional coordinate points to obtain three-dimensional coordinate points corresponding to the auxiliary feature points in each frame of image to be processed, and the three-dimensional coordinate points corresponding to the auxiliary feature points in the plurality of frames of images to be processed are registered to obtain the three-dimensional coordinate points for the auxiliary feature points in the plurality of frames of images to be processed in the same coordinate system. The above two methods are only examples for performing processing based on a plurality of frames of images to be processed to obtain three-dimensional coordinate points in the same coordinate system. Some embodiments of the present disclosure does not limit a specific method for performing processing based on a plurality of frames of images to be processed to obtain three-dimensional coordinate points in the same coordinate system.

In some embodiments of the present disclosure, after the plurality of frames of images to be processed are obtained, processing can be performed based on the plurality of frames of images to be processed to obtain the three-dimensional coordinate points in the same coordinate system.

Step 103: Measurement processing is performed on the three-dimensional coordinate points to obtain target three-dimensional coordinate points.

The target three-dimensional coordinate points refer to three-dimensional coordinate points obtained after performing measurement processing on the three-dimensional coordinate points, which can more accurately reflect the three-dimensional coordinate points of the auxiliary feature points.

In some embodiments of the present disclosure, there are various methods for performing measurement processing on all the three-dimensional coordinate points to obtain target three-dimensional coordinate points. In some implementations, each of the three-dimensional coordinate points is projected to an image coordinate system to obtain a two-dimensional pixel coordinate point. When the Euclidean distance between the two-dimensional pixel coordinate point and the two-dimensional coordinate point corresponding to the three-dimensional coordinate point is minimized, the three-dimensional coordinate point is taken as the target three-dimensional coordinate point.

In some other embodiments, an $N^{th}$ frame of image where three-dimensional coordinate points appear is obtained, two-dimensional pixel coordinate points of the $N^{th}$ frame of image are obtained, and target three-dimensional coordinate points are determined based on the distance between two-dimensional coordinate points projected by the three-dimensional coordinate points and the two-dimensional pixel coordinate points, where N is a positive integer. The above two methods are only examples for performing measurement processing on all the three-dimensional coordinate points to obtain target three-dimensional coordinate points. Some embodiments of the present disclosure does not limit a specific method for performing measurement processing on all the three-dimensional coordinate points to obtain target three-dimensional coordinate points.

In some embodiments, after all the three-dimensional coordinate points are obtained, measurement processing can be performed on all the three-dimensional coordinate points to obtain the target three-dimensional coordinate points.

Step 104: A target position transformation relationship is determined based on the target three-dimensional coordinate points and the distribution true values.

The target position transformation relationship refers to a transformation matrix that converts the target three-dimensional coordinate points obtained through scanning into the distribution true values corresponding to the design.

In some embodiments of the present disclosure, there are various methods for determining a target position transformation relationship based on the target three-dimensional coordinate points and the distribution true values. In some implementations, an initial position transformation relationship is obtained through calculation based on a preset scaling factor, target three-dimensional coordinate points, and distribution true values, optimization calculation is performed on the scaling factor, the target three-dimensional coordinate points, the distribution true values, and the initial position transformation relationship based on a preset optimization formula to obtain an optimized value, and the scaling factor and the initial position transformation relationship are adjusted to obtain a corresponding initial position transformation relationship as the target position transformation relationship when the optimized value is less than a preset threshold.

In some other implementations, a position transformation relationship from each target three-dimensional coordinate point to the distribution true value is calculated, and the target position transformation relationship is obtained based on the plurality of position transformation relationships. The above two methods are only examples for determining a target position transformation relationship based on the target three-dimensional coordinate points and the distribution true values. Some embodiments of the present disclosure do not limit a specific method for determining a target position transformation relationship based on the target three-dimensional coordinate points and the distribution true values.

According to the solution for processing scanning data provided by some embodiments of the present disclosure, the plurality of frames of images to be processed are obtained. Each frame of image to be processed includes the auxiliary feature points. The auxiliary feature points have the corresponding distribution true values. Processing is performed based on the plurality of frames of images to be processed to obtain all the three-dimensional coordinate points. Measurement processing is performed on all the three-dimensional coordinate points to obtain the target three-dimensional coordinate points. Based on the target three-dimensional coordinate points and the distribution true values, the target position transformation relationship is determined. By adopting the above technical solution, the target position transformation relationship is determined based on the distribution true values preset for the auxiliary feature points and the three-dimensional coordinate points calculated through scanning, such that a relative position between scan posts can be accurately located, and the data processing efficiency and accuracy in an intraoral scanning scenario are improved.

Figure 3:
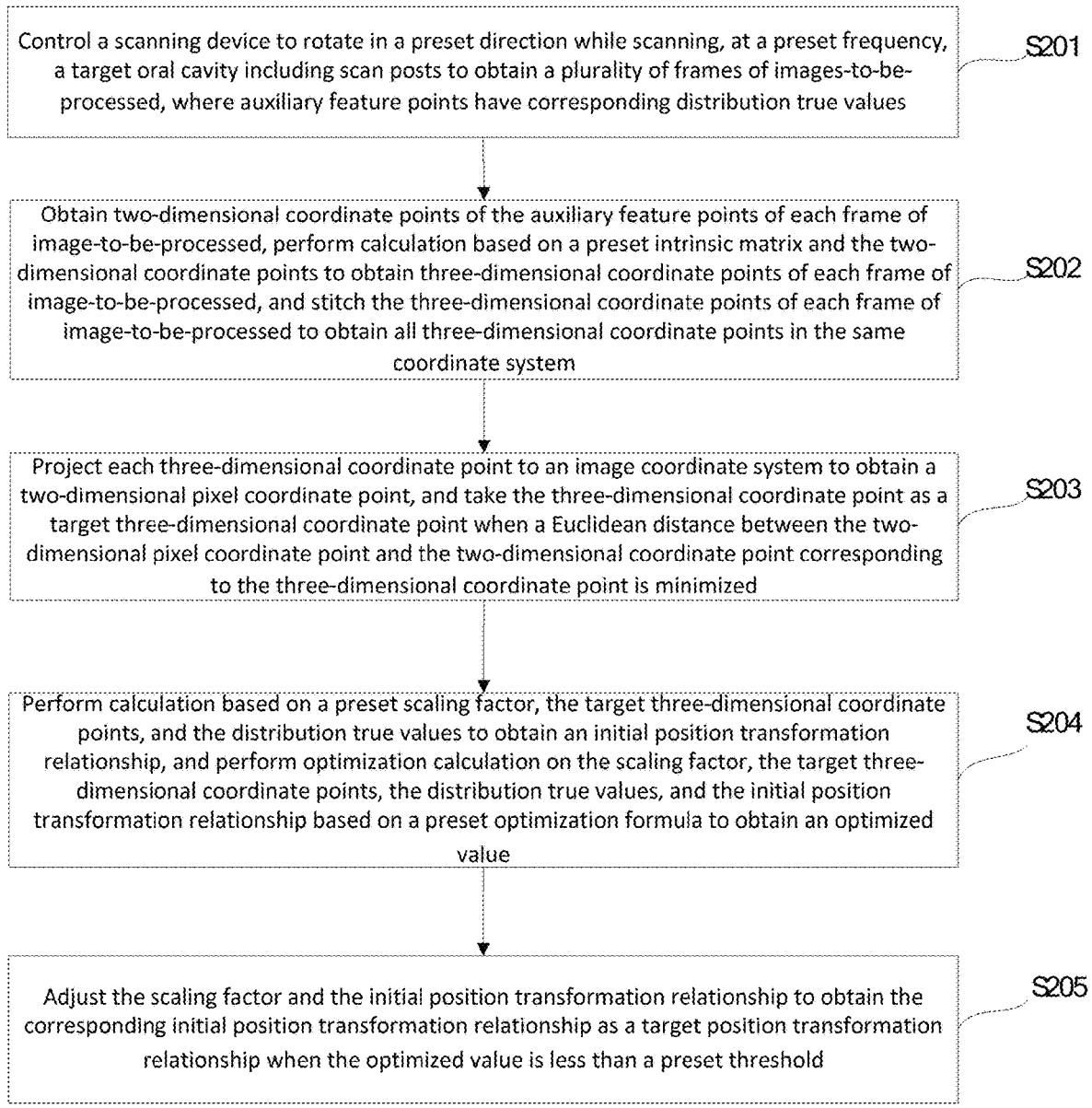
FIG. 3 is a schematic flowchart of another method for processing scanning data according to an embodiment of the present disclosure.
Figure 4:
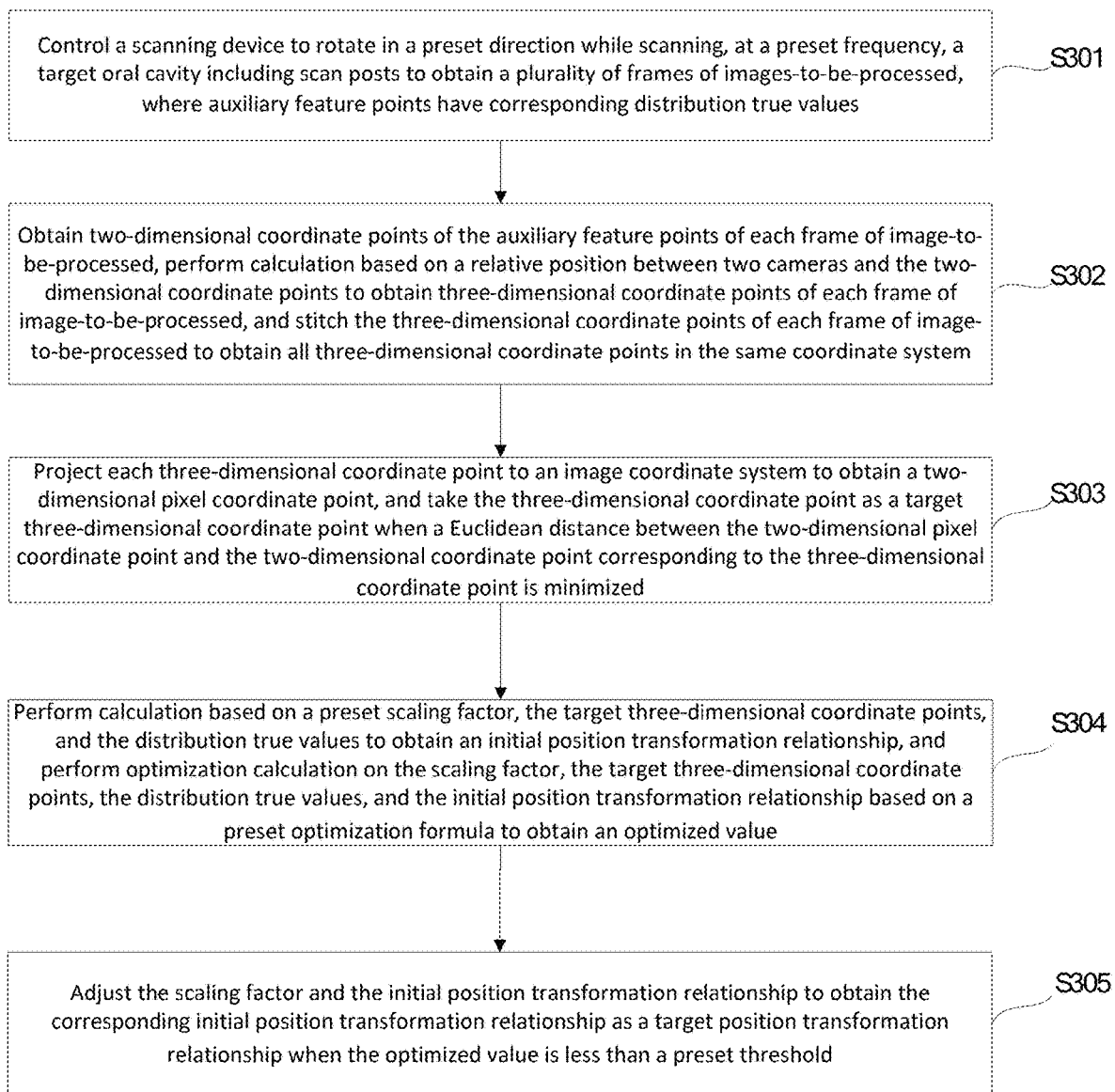
FIG. 4 is a schematic flowchart of another method for processing scanning data according to an embodiment of the present disclosure.

Based on the description of the above embodiment, scanning can be performed through the monocular camera and the binocular camera, and the monocular camera and the binocular camera are respectively described in detail in conjunction with FIG. 3 and FIG. 4.

In some embodiments, FIG. 3 is a schematic flowchart of a method for processing scanning data according to an embodiment of the present disclosure. In some embodiments, the above method for processing scanning data is further optimized based on the above embodiment. As shown in FIG. 3, the method includes the following steps:

Step 201: A scanning device is controlled to rotate in a preset direction while scanning, at a preset frequency, a target oral cavity including scan posts to obtain a plurality of frames of images to be processed, where auxiliary feature points have corresponding distribution true values.

In some embodiments, a monocular camera is controlled to rotate in a specific direction while scanning the target oral cavity at a specific frequency to obtain a plurality of frames of images to be processed. Alternatively, a binocular camera is controlled to cyclically scan the target oral cavity to obtain a plurality of frames of images to be processed.

Step 202: Two-dimensional coordinate points of the auxiliary feature points of each frame of image to be processed are obtained, calculation is performed based on a preset intrinsic matrix and the two-dimensional coordinate points to obtain three-dimensional coordinate points of each frame of image to be processed, and the three-dimensional coordinate points of each frame of image to be processed are registered to obtain all three-dimensional coordinate points in the same coordinate system.

In some embodiments, the plurality of frames of images to be processed is obtained through scanning (e.g., triggering by hardware to collect dozens of frames of images to be processed per second in a photography manner, and performing cyclic acquisition). Based on the images to be processed, the two-dimensional coordinate points of the auxiliary feature points in each frame of image to be processed are obtained (i.e., extracting pixel coordinates of the auxiliary feature points of each frame of image to be processed in an image recognition processing manner). Based on camera intrinsic parameters (e.g., focal length, principal point, skew factor, and lens distortion), a texture tracked pose (e.g., registering adjacent frames by obtaining geometric and texture information of a surface of the scan post), reconstruction of the auxiliary feature points in the current frame is completed, and the reconstructed three-dimensional coordinate points are based on a first-frame camera coordinate system during scanning (the first-frame camera coordinate system is determined by the first frame of image, each of subsequent frames is registered with the first frame, and therefore the coordinate system remains the same as the first-frame camera coordinate system; and the two-dimensional coordinate points are recognized from the image, and need to be converted to the camera coordinate system to obtain the three-dimensional coordinate points).

The intrinsic matrix refers to a matrix composed of the camera intrinsic parameters; such that the two-dimensional coordinate points are back projected to the camera coordinate system based on the intrinsic matrix to obtain the three-dimensional coordinate points.

In some embodiments, the three-dimensional coordinate points of each frame of image to be processed are registered to obtain all three-dimensional coordinate points. Based on a preset registering algorithm, the two frames of different coordinate systems can be aligned through common parts and then registered, thereby obtaining all three-dimensional coordinate points. That is, the three-dimensional coordinate points reconstructed from all the single frames are fused into an overall framework of points based on distance constraints, namely, all three-dimensional coordinate points, and the all three-dimensional coordinate points are based on an overall dental model coordinate system (world coordinate system).

Step 203: Each three-dimensional coordinate point is projected to an image coordinate system to obtain a two-dimensional pixel coordinate point, and the three-dimensional coordinate point is taken as a target three-dimensional coordinate point when the Euclidean distance between the two-dimensional pixel coordinate point and the two-dimensional coordinate point corresponding to the three-dimensional coordinate point is minimized.

In some embodiments, assuming that a $K^{th}$ auxiliary feature point $p3D_k$ appears in an $i^{th}$ frame of image and corresponds to a $j^{th}$ two-dimensional coordinate point $p2D_j$ in an $i^{th}$ frame of texture image (it is possible to trigger acquisition of black and white images and texture images with color information at the same time). Photogrammetry optimization is based on the bundle adjustment theory and the least squares theory. The optimization goal is to minimize the Euclidean distance between two-dimensional pixel coordinates of all actually scanned auxiliary feature points projected to each frame of captured image based on the image frame number where the actually scanned auxiliary feature points appear and a camera pose $T_i$ (a projection function is defined as $\Pi$) and corresponding two-dimensional coordinate points of the auxiliary feature points, and calculation is shown in a formula (1):

$$\min f(p3D, T) = \min\left(\sum_{k=0}^{k=m}\sum_{i=0}^{i=n}\sum_{j=0}^{j=l}(\prod(T_i^{-1}p3D_k) - p2D_j)\right) \quad (1)$$

where m denotes the number of the three-dimensional coordinate points, and n denotes the number of the images to be processed.

Step 204: Calculation is performed based on a preset scaling factor, the target three-dimensional coordinate points, and the distribution true values to obtain an initial position transformation relationship, and optimization calculation is performed on the scaling factor, the target three-dimensional coordinate points, the distribution true values, and the initial position transformation relationship based on a preset optimization formula to obtain an optimized value.

Step 205: The scaling factor and the initial position transformation relationship are adjusted to obtain the corresponding initial position transformation relationship as the target position transformation relationship when the optimized value is less than a preset threshold.

In some embodiments, based on the distribution true value of the auxiliary feature point on the scan post or an auxiliary feature body connected to the scan post (e.g., a single-lens reflex photogrammetry system, a two-dimensional imager, etc. acquire the distribution true value of the auxiliary feature point), which is denoted by $q_i$, the target three-dimensional coordinate point P obtained after the photogrammetry optimization and the distribution true values of the auxiliary feature points of various regions (each scan post may be considered as a small region) are registered with scaling (registering is rigid body without changing a scale, and when the scale changes, a $S_i$ scaling factor is introduced for calculation), so as to determine a target position transformation relationship of different scan posts, and minf ( ) refers to a nonlinear least squares algorithm, which is specifically shown in a formula (2):

$$\min f(s_i, R_i, t_i) = s_i * R_i * p + t_i - q_i \quad (2)$$

In some embodiments, assuming that $S_i=1$ (the true value may be between 0.9 and 1.1), initial ($R_i$, $t_i$) is calculated through P and $q_i$, and finally, the assumed $S_i$ and the initial ($R_i$, $t_i$) are optimized together. The optimization goal is to ensure that after scaling the point P with $S_i$, the point P and $q_i$ can be right registered through the initial ($R_i$, $t_i$), and the entire optimization is a process of mathematical iteration that $S_i$ and ($R_i$, $t_i$) are continuously adjusted to make the registered two points of P and $q_i$ infinitely close.

Therefore, by scanning the entire oral cavity, the relative position between the scan posts can be accurately located.

According to the solution for processing scanning data provided by some embodiments of the present disclosure, the plurality of frames of images to be processed including the auxiliary feature points are obtained. The auxiliary feature points have the corresponding distribution true values. The two-dimensional coordinate points of the auxiliary feature points of each frame of image to be processed are obtained. Calculation is performed based on the preset intrinsic matrix and the two-dimensional coordinate points to obtain the three-dimensional coordinate points of each frame of image to be processed. The three-dimensional coordinate points of each frame of image to be processed are registered to obtain all the three-dimensional coordinate points in the same coordinate system. Each three-dimensional coordinate point is projected to the image coordinate system to obtain the two-dimensional pixel coordinate point, and the three-dimensional coordinate point is taken as the target three-dimensional coordinate point when the Euclidean distance between the two-dimensional pixel coordinate point and the two-dimensional coordinate point corresponding to the three-dimensional coordinate point is minimized. Calculation is performed based on the preset scaling factor, the target three-dimensional coordinate points, and the distribution true values to obtain the initial position transformation relationship, and optimization calculation is performed on the scaling factor, the target three-dimensional coordinate points, the distribution true values, and the initial position transformation relationship based on the preset optimization formula to obtain the optimized value. The scaling factor and the initial position transformation relationship are adjusted to obtain the corresponding initial position transformation relationship as the target position transformation relationship when the optimized value is less than the preset threshold. Therefore, the target position transformation relationship is determined based on the distribution true values preset for the auxiliary feature points and the three-dimensional coordinate points calculated through scanning, such that the relative position between the scan posts can be accurately located, and the data processing efficiency and accuracy in the intraoral scanning scenario are improved.

In some embodiments, FIG. 4 is a schematic flowchart of another method for processing scanning data according to an embodiment of the present disclosure. In some embodiments, the above method for processing scanning data is further optimized based on the above embodiment. As shown in FIG. 4, the method includes the following steps:

Step 301: A scanning device is controlled to rotate in a preset direction while scanning, at a preset frequency, a target oral cavity including scan posts to obtain a plurality of frames of images to be processed, where auxiliary feature points have corresponding distribution true values.

In some embodiments, a monocular camera is controlled to rotate in a specific direction while scanning the target oral cavity at a specific frequency to obtain a plurality of frames of images to be processed. Alternatively, a binocular camera is controlled to cyclically scan the target oral cavity to obtain a plurality of frames of images to be processed.

Step 302: Two-dimensional coordinate points of the auxiliary feature points of each frame of image to be processed are obtained, calculation is performed based on a relative position between two cameras and the two-dimensional coordinate points to obtain three-dimensional coordinate points of each frame of image to be processed, and the three-dimensional coordinate points of each frame of image to be processed are registered to obtain all three-dimensional coordinate points in the same coordinate system.

In some embodiments, the images to be processed are obtained through scanning, and the two-dimensional coordinate points of the auxiliary feature points in each frame of image to be processed are obtained based on the images to be processed. Based on the relative position between the two cameras, the three-dimensional coordinate points of the auxiliary feature points in each frame are reconstructed, and the reconstructed three-dimensional coordinate points are based on a current-frame left-camera coordinate system (typically, reconstructed depth information is based on the left-camera coordinate system).

In some embodiments, based on the reconstructed three-dimensional coordinate points of the auxiliary feature points in each frame and distance distribution information of the auxiliary feature points in adjacent frames (performing distance calculation based on the coordinate points of the pairs of auxiliary feature points), the same auxiliary feature point captured in the adjacent frames is searched for, and registering of the auxiliary feature points is completed, thereby obtaining all three-dimensional coordinate points. That is, the three-dimensional coordinate points reconstructed from all the single frames are fused into an overall framework of points based on distance constraints, namely, all three-dimensional coordinate points, and the all three-dimensional coordinate points are based on an overall dental model coordinate system (world coordinate system).

Step 303: Each three-dimensional coordinate point is projected to an image coordinate system to obtain a two-dimensional pixel coordinate point, and the three-dimensional coordinate point is taken as a target three-dimensional coordinate point when the Euclidean distance between the two-dimensional pixel coordinate point and the two-dimensional coordinate point corresponding to the three-dimensional coordinate point is minimized.

In some embodiments, assuming that a $K^{th}$ auxiliary feature point $p3D_k$ appears in an $i^{th}$ frame and corresponds to a $j^{th}$ two-dimensional point $p2DL_j$, $p2DR_j$ in an $i^{th}$ frame of texture image, and rigid body transformation between the two cameras is $T_{RL}$. Photogrammetry optimization is based on the bundle adjustment theory. The optimization goal is to minimize the Euclidean distance between two-dimensional pixel coordinates of all actually scanned auxiliary feature points projected to each frame of captured image based on the image frame number where the actually scanned auxiliary feature points appear and a camera pose $T_i$ (a projection function is defined $\Pi$) and corresponding two-dimensional coordinate points of the auxiliary feature points, and calculation is shown in a formula (3):

$$\min f(p3D, T) = \min \left( \sum_{k=0}^{k=m} \sum_{i=0}^{i=n} \sum_{j=0}^{j=l} \left( \prod_L \left( T_i^{-1} p3D_k \right) - p2DL_j \right) + \prod_R \left( T_{RL} T_i^{-1} p3D_k \right) - p2DR_j \right) \quad (3)$$

where m denotes the number of the three-dimensional coordinate points, and n denotes the number of the images to be processed.

Step 304: Calculation is performed based on a preset scaling factor, the target three-dimensional coordinate points, and the distribution true values to obtain an initial position transformation relationship, and optimization calculation is performed on the scaling factor, the target three-dimensional coordinate points, the distribution true values, and the initial position transformation relationship based on a preset optimization formula to obtain an optimized value.

Step 305: The scaling factor and the initial position transformation relationship are adjusted to obtain the corresponding initial position transformation relationship as the target position transformation relationship when the optimized value is less than a preset threshold.

In some embodiments, based on the distribution true value of the auxiliary feature point on the scan post or an auxiliary feature body connected to the scan post (e.g., a single-lens reflex photogrammetry system, a two-dimensional imager, etc. acquire the distribution true value of the auxiliary feature point), which is denoted by $q_i$, the target three-dimensional coordinate point P obtained after the photogrammetry optimization and the distribution true values of the auxiliary feature points of various regions (each scan post may be considered as a small region) are registered with scaling (registering is rigid body without changing a scale, and when the scale changes, a $S_i$ scaling factor is introduced for calculation), so as to determine a target position transformation relationship of different scan posts, and minf ( ) refers to a nonlinear least squares algorithm, which is specifically shown in a formula (2):

$$\min f(s_i, R_i, t_i) = s_i * R_i * p + t_i - q_i \quad (2)$$

In some embodiments, assuming that $S_i=1$ (the true value may be between 0.9 and 1.1), initial ($R_i$, $t_i$) is calculated through P and $q_i$, and finally, the assumed $S_i$ and the initial ($R_i$, $t_i$) are optimized together. The optimization goal is to ensure that after scaling the point P with $S_i$, the point P and $q_i$ can be right registered through the initial ($R_i$, $t_i$), and the entire optimization is a process of mathematical iteration that $S_i$ and ($R_i$, $t_i$) are continuously adjusted to make the registered two points of P and $q_i$ infinitely close.

Therefore, by scanning the entire oral cavity, the relative position between the scan posts can be accurately located.

According to the solution for processing scanning data provided by some embodiments of the present disclosure, the plurality of frames of images to be processed including the auxiliary feature points are obtained. The auxiliary feature points have the corresponding distribution true values. The two-dimensional coordinate points of the auxiliary feature points of each frame of image to be processed are obtained. Calculation is performed based on the relative position between the two cameras and the two-dimensional coordinate points to obtain the three-dimensional coordinate points of each frame of image to be processed. The three-dimensional coordinate points of each frame of image to be processed are registered to obtain all the three-dimensional coordinate points in the same coordinate system. Each three-dimensional coordinate point is projected to the image coordinate system to obtain the two-dimensional pixel coordinate point, and the three-dimensional coordinate point is taken as the target three-dimensional coordinate point when the Euclidean distance between the two-dimensional pixel coordinate point and the two-dimensional coordinate point corresponding to the three-dimensional coordinate point is minimized. Calculation is performed based on the preset scaling factor, the target three-dimensional coordinate points, and the distribution true values to obtain the initial position transformation relationship, and optimization calculation is performed on the scaling factor, the target three-dimensional coordinate points, the distribution true values, and the initial position transformation relationship based on the preset optimization formula to obtain the optimized value. The scaling factor and the initial position transformation relationship are adjusted to obtain the corresponding initial position transformation relationship as the target position transformation relationship when the optimized value is less than the preset threshold. Therefore, the target position transformation relationship is determined based on the distribution true values preset for the auxiliary feature points and the three-dimensional coordinate points calculated through scanning, such that the relative position between the scan posts can be accurately located, and the data processing efficiency and accuracy in the intraoral scanning scenario are improved.

Figure 5:
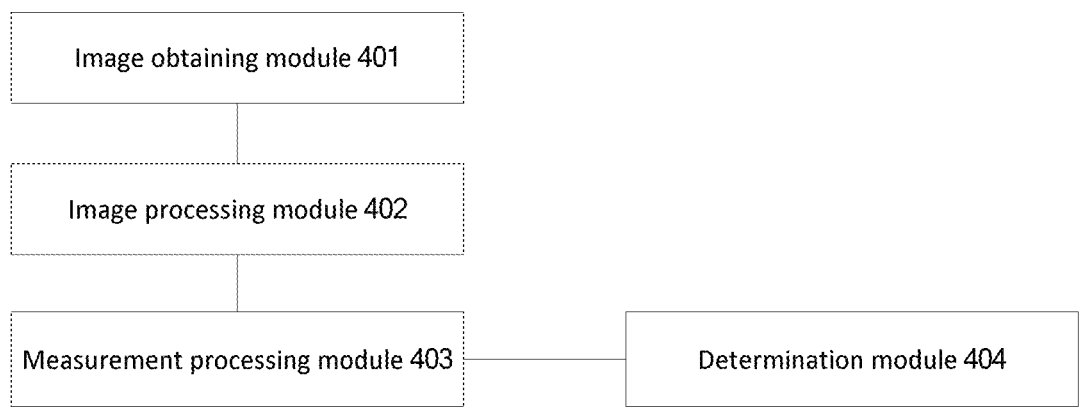
FIG. 5 is a schematic structural diagram of an apparatus for processing scanning data according to an embodiment of the present disclosure.

FIG. 5 is a schematic structural diagram of an apparatus for processing scanning data according to an embodiment of the present disclosure. The apparatus can be implemented by software and/or hardware, and can be typically integrated in an electronic device. As shown in FIG. 5, the apparatus includes:

an image obtaining component 401, configured to obtain a plurality of frames of images to be processed, wherein each frame of images to be processed comprises auxiliary feature points, where the auxiliary feature points have corresponding distribution true values;

an image processing component 402, configured to perform processing based on the plurality of frames of images to be processed to obtain all three-dimensional coordinate points in a same coordinate system;

a measurement processing component 403, configured to perform measurement processing on all the three-dimensional coordinate points to obtain target three-dimensional coordinate points; and a determination component 404, configured to determine a target position transformation relationship based on the target three-dimensional coordinate points and the distribution true values.

In some embodiments, the image processing component 402 is specifically configured to:

obtain two-dimensional coordinate points of the auxiliary feature points in each frame of image to be processed;

perform calculation based on a preset intrinsic matrix and the two-dimensional coordinate points to obtain three-dimensional coordinate points of each frame of image to be processed; and register the three-dimensional coordinate points of each frame of image to be processed to obtain all the three-dimensional coordinate points in the same coordinate system.

In some embodiments, the image processing component 402 is specifically configured to:

obtain two-dimensional coordinate points of the auxiliary feature points in each frame of image to be processed;

perform calculation based on a relative position between two cameras and the two-dimensional coordinate points to obtain three-dimensional coordinate points of each frame of image to be processed; and register the three-dimensional coordinate points of each frame of image to be processed to obtain all the three-dimensional coordinate points in the same coordinate system.

In some embodiments, the measurement processing component 403 is specifically configured to:

project each of the three-dimensional coordinate points to an image coordinate system to obtain a two-dimensional pixel coordinate point; and take the three-dimensional coordinate point as the target three-dimensional coordinate point when a Euclidean distance between the two-dimensional pixel coordinate point and a two-dimensional coordinate point corresponding to the three-dimensional coordinate point is minimized.

In some embodiments, the determination component 404 is specifically configured to:

perform calculation based on a preset scaling factor, the target three-dimensional coordinate points, and the distribution true values to obtain an initial position transformation relationship;

perform optimization calculation on the scaling factor, the target three-dimensional coordinate points, the distribution true values, and the initial position transformation relationship based on a preset optimization formula to obtain an optimized value; and adjust the scaling factor and the initial position transformation relationship to obtain the corresponding initial position transformation relationship as the target position transformation relationship when the optimized value is less than a preset threshold.

In some embodiments, the image obtaining component 401 is specifically configured to:

control a scanning device to rotate in a preset direction while scanning, at a preset frequency, a target oral cavity including scan posts to obtain the plurality of frames of images to be processed.

The apparatus for processing scanning data provided by some embodiments of the present disclosure can execute the method for processing scanning data provided by any embodiment of the present disclosure, and has corresponding functional components and beneficial effects for executing the method.

An embodiment of the present disclosure further provides a computer program product including computer programs/instructions. The computer programs/instructions, when executed by a processor, implement the method for processing scanning data provided by any embodiment of the present disclosure.

Figure 6:
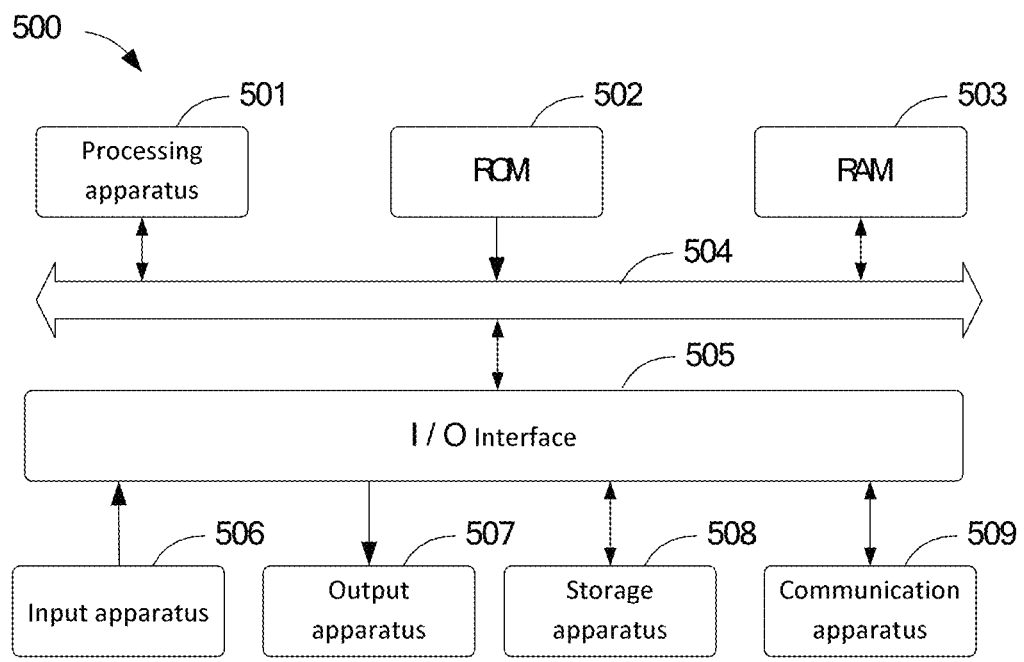
FIG. 6 is a schematic structural diagram of an electronic device according to an embodiment of the present disclosure.

FIG. 6 is a schematic structural diagram of an electronic device according to an embodiment of the present disclosure. Specifically referring to FIG. 6 below, FIG. 6 illustrates a schematic structural diagram of an electronic device 500 suitable for implementing an embodiment of the present disclosure. The electronic device 500 in some embodiments of the present disclosure may include, but is not limited to, mobile terminals such as a mobile phone, a notebook computer, a digital radio receiver, a personal digital assistant (PDA), a portable Android device (PAD), a portable media player (PMP), a vehicle-mounted terminal (e.g., a vehicle-mounted navigation terminal), and fixed terminals such as a digital TV and a desktop computer. The electronic device shown in FIG. 6 is merely an example, which should not impose any limitations on functions and application ranges of some embodiments of the present disclosure.

As shown in FIG. 6, the electronic device 500 may include a processing apparatus (e.g., a central processing unit and a graphics processing unit) 501, which may perform various appropriate actions and processing according to programs stored on a read only memory (ROM) 502 or loaded from a storage apparatus 508 into a random access memory (RAM) 503. The RAM 503 further stores various programs and data required for the operation of the electronic device 500. The processing apparatus 501, the ROM 502, and the RAM 503 are connected to one another through a bus 504. An input/output (I/O) interface 505 is also connected to the bus 504.

Typically, the following apparatuses may be connected to the I/O interface 505: an input apparatus 506, including, for example, a touchscreen, a touchpad, a keyboard, a mouse, a camera, a microphone, an accelerometer, and a gyroscope; an output apparatus 507, including, for example, a liquid crystal display (LCD), a speaker, and a vibrator; the storage apparatus 508, including, for example, a magnetic tape and a hard disk; and a communication apparatus 509. The communication apparatus 509 may allow the electronic device 500 to be in wireless or wired communication with other devices for data exchange. Although FIG. 6 illustrates the electronic device 500 with various apparatuses, it is to be understood that it is not necessary to implement or have all the shown apparatuses. Alternatively, more or fewer apparatuses may be implemented or provided.

Particularly, the foregoing process described with reference to the flowchart according to the embodiments of the present disclosure may be implemented as a computer software program. For example, an embodiment of the present disclosure includes a computer program product including a computer program carried on a non-transitory computer-readable medium. The computer program includes program code for executing the method shown in the flowchart. In such an embodiment, the computer program may be downloaded and installed from a network by the communication apparatus 509, or installed from the storage apparatus 508, or installed from the ROM 502. The computer program, when executed by the processing apparatus 501, implements the above functions defined in the method for processing scanning data according to some embodiments of the present disclosure.

It should be noted that the computer-readable medium in the present disclosure may be a computer-readable signal medium, or a computer-readable storage medium, or any combination thereof. For example, the computer-readable storage medium may include, but is not limited to: electrical, magnetic, optical, electromagnetic, infrared, or semiconductor systems, apparatuses, or devices, or any combination thereof. More specific examples of the computer-readable storage medium may include, but are not limited to: an electrical connection with one or more wires, a portable computer disk, a hard disk, a random access memory (RAM), a read only memory (ROM), an erasable programmable read only memory (EPROM or a flash memory), fiber optics, a portable compact disc read only memory (CD-ROM), an optical storage device, a magnetic storage device, or any proper combination of the above. In the present disclosure, the computer-readable storage medium may be any tangible medium including or storing a program, and the program may be used by an instruction execution system, apparatus, or device, or used in conjunction with the instruction execution system, apparatus, or device. However, in the present disclosure, the computer-readable signal medium may include data signals propagated in a baseband or propagated as a part of a carrier wave, which carry computer-readable program code. The propagated data signals may have a plurality of forms, including, but not limited to, electromagnetic signals, optical signals, or any proper combination of the above. The computer-readable signal medium may be any computer-readable medium other than the computer-readable storage medium. The computer-readable signal medium may send, propagate, or transmit the program used by the instruction execution system, apparatus, or device, or used in conjunction with the instruction execution system, apparatus, or device. The program code included in the computer-readable medium may be transmitted by any proper medium including, but not limited to, a wire, an optical cable, radio frequency (RF), etc., or any proper combination of the above.

In some implementations, a client and a server can communicate using any currently known or future-developed network protocols such as a hyper text transfer protocol (HTTP), and may also be in communication connection with digital data in any form or medium (e.g., a communication network). For example, examples of the communication network include a local area network ("LAN"), a wide area network ("WAN"), Internet work (e.g., Internet), a peer-to-peer network (e.g., an ad hoc peer-to-peer network), and any currently known or future-developed networks.

The computer-readable medium may be included in the electronic device; and may separately exist without being assembled in the electronic device.

The computer-readable medium carries one or more programs. The one or more programs, when executed by the electronic device, enable the electronic device to: receive an information display trigger operation of a user in a video playing process; acquire at least two pieces of target information associated with a video; display first target information from the at least two pieces of target information in an information display region of a video playing page, where the size of the information display region is less than that of the playing page; and receive a first switching trigger operation of the user, and switch the first target information displayed in the information display region into second target information from the at least two pieces of target information.

The computer program code for executing the operations of the present disclosure may be written in one or more programming languages or a combination thereof. The programming languages include, but not limited to, object-oriented programming languages such as Java, Smalltalk, C++, as well as conventional procedural programming languages such as "C" or similar programming languages. The program code may be executed entirely or partially on a user computer, executed as a standalone software package, executed partially on the user computer and partially on a remote computer, or executed entirely on the remote computer or a server. In the case of involving the remote computer, the remote computer may be connected to the user computer via any type of network, including a local area network (LAN) or wide area network (WAN), or may be connected to an external computer (e.g., utilizing an Internet service provider for Internet connectivity).

The flowcharts and block diagrams in the accompanying drawings illustrate system architectures, functions, and operations possibly implemented by the system, method and computer program product according to the various embodiments of the present disclosure. In this regard, each block in the flowcharts or block diagrams may represent a module, a program segment, or a portion of code, and the module, program segment, or portion of code includes one or more executable instructions for implementing specified logical functions. It should be noted that in some alternative implementations, functions marked in the blocks may also occur in an order different from that marked in the accompanying drawings. For example, two consecutively-shown blocks may be actually executed in parallel basically, but sometimes may also be executed in a reverse order, which depends on involved functions. It should be further noted that each block in the block diagrams and/or flowcharts as well as a combination of the blocks in the block diagrams and/or flowcharts may be implemented by using a dedicated hardware-based system that executes specified functions or operations, or using a combination of special hardware and computer instructions.

The units described in the embodiments of the present disclosure may be implemented through software or hardware. The name of the unit does not limit the unit in certain cases.

The functions described herein above may be at least partially executed by one or more hardware logic components. For example, exemplary hardware logic components that can be used include, but not limited to, a field-programmable gate array (FPGA), an application specific integrated circuit (ASIC), an application specific standard part (ASSP), a system on chip (SOC), a complex programmable logic device (CPLD), etc.

In the context of the present disclosure, a machine-readable medium may be a tangible medium that may contain or store a program for use by the instruction execution system, apparatus, or device, or in conjunction with the instruction execution system, apparatus, or device. The machine-readable medium may be a machine-readable signal medium or a machine-readable storage medium. The machine-readable medium may include, but is not limited to: electronic, magnetic, optical, electromagnetic, infrared, or semiconductor systems, apparatuses, or devices, or any proper combination of the above. More specific examples of the machine-readable storage medium may include: an electrical connection based on one or more wires, a portable computer disk, a hard drive, a random access memory (RAM), a read only memory (ROM), an erasable programmable read only memory (EPROM or a flash memory), fiber optics, a portable compact disc read only memory (CD-ROM), an optical storage device, a magnetic storage device, or any proper combination of the above.

According to one or more embodiments of the present disclosure, the present disclosure provides an electronic device, including:
  a processor; and
  a memory configured to store executable instructions of the processor.

The processor is configured to read the executable instructions from the memory, and execute the instructions to implement any one of the methods for processing scanning data provided by the present disclosure.

According to one or more embodiments of the present disclosure, the present disclosure provides a computer-readable storage medium. The storage medium stores a computer program. The computer program is configured to execute any one of the methods for processing scanning data provided by the present disclosure.

It should be noted that herein, relational terms such as "first" and "second" are used only to distinguish one entity or operation from another and do not necessarily require or imply any actual relationship or order between these entities or operations. In addition, terms "comprise", "include" or any other variations thereof are intended to cover non-exclusive inclusion, and therefore a process, a method, an article, or a device including a series of elements not only includes those elements but also includes other elements not clearly listed, or further includes inherent elements for the process, the method, the article, or the device. In the absence of further restrictions, an element specified by the phrase "including a . . . " does not exclude the existence of other identical elements in the process, method, article, or, device that includes the element.

The above contents are merely specific implementations of the present disclosure, such that those skilled in the art can understand or implement the present disclosure. More modifications to these embodiments are apparent to those skilled in the art, and general principles defined herein may be implemented in other embodiments without departing from the spirit or scope of the present disclosure. Thus, the present disclosure will not be limited by these embodiments shown herein but is required to conform to a widest scope consistent with the principles and novel characteristics disclosed herein.

INDUSTRIAL APPLICABILITY

According to the solution for processing scanning data disclosed by the present disclosure, the target position transformation relationship is determined based on the distribution true values preset for the auxiliary feature points and the three-dimensional coordinate points calculated through scanning, such that the relative position between the scan posts can be accurately located, the data processing efficiency and accuracy in the intraoral scanning scenario are improved, and industrial applicability is high.

What is claimed is:
1. A method for processing scanning data, comprising:
  obtaining a plurality of frames of images to be processed, wherein each frame of images to be processed comprises auxiliary feature points, the auxiliary feature points have corresponding distribution true values;
  performing processing based on the plurality of frames of images to be processed to obtain three-dimensional coordinate points of the auxiliary feature points in a same coordinate system;
  performing measurement processing on the three-dimensional coordinate points of the auxiliary feature points to obtain target three-dimensional coordinate points; and
  determining a target position transformation relationship based on the target three-dimensional coordinate points and the distribution true values.

2. The method for processing scanning data as claimed in claim 1, wherein the performing processing based on the plurality of frames of images to be processed to obtain the three-dimensional coordinate points of the auxiliary feature points in the same coordinate system comprises:
  obtaining two-dimensional coordinate points of the auxiliary feature points in each frame of image to be processed;
  performing calculation based on a preset intrinsic matrix and the two-dimensional coordinate points to obtain three-dimensional coordinate points of each frame of image to be processed; and
  registering the three-dimensional coordinate points of each frame of image to be processed to obtain the three-dimensional coordinate points of the auxiliary feature points in the same coordinate system.

3. The method for processing scanning data as claimed in claim 1, wherein the performing processing based on the plurality of frames of images to be processed to obtain the three-dimensional coordinate points of the auxiliary feature points in the same coordinate system comprises:
  obtaining two-dimensional coordinate points of the auxiliary feature points in each frame of image to be processed;
  performing calculation based on the two-dimensional coordinate points and a relative position between two cameras to obtain three-dimensional coordinate points of each frame of image to be processed; and
  registering the three-dimensional coordinate points of each frame of image to be processed to obtain the three-dimensional coordinate points of the auxiliary feature points in the same coordinate system.

4. The method for processing scanning data as claimed in claim 1, wherein the performing the measurement processing on the three-dimensional coordinate points of the auxiliary feature points to obtain the target three-dimensional coordinate points comprises:
  projecting each of the three-dimensional coordinate points to an image coordinate system to obtain a two-dimensional pixel coordinate point; and
  taking the three-dimensional coordinate point as the target three-dimensional coordinate point when a Euclidean distance between the two-dimensional pixel coordinate point and a two-dimensional coordinate point corresponding to the three-dimensional coordinate point is minimized.

5. The method for processing scanning data as claimed in claim 1, wherein the determining the target position transformation relationship based on the target three-dimensional coordinate points and the distribution true values comprises:
  performing calculation based on a preset scaling factor, the target three-dimensional coordinate points, and the distribution true values to obtain an initial position transformation relationship;
  performing optimization calculation on the scaling factor, the target three-dimensional coordinate points, the distribution true values, and the initial position transformation relationship based on a preset optimization formula to obtain an optimized value; and adjusting the scaling factor and the initial position transformation relationship to obtain the corresponding initial position transformation relationship as the target position transformation relationship when the optimized value is less than a preset threshold.

6. The method for processing scanning data as claimed in claim 1, wherein the obtaining the plurality of frames of images to be processed comprising auxiliary feature points comprises:

controlling a scanning device to rotate in a preset direction while scanning, at a preset frequency, a target oral cavity comprising scan posts to obtain the plurality of frames of images to be processed.

7. An apparatus for processing scanning data, comprising:

an image obtaining component, configured to obtain a plurality of frames of images to be processed, wherein each frame of images to be processed comprises auxiliary feature points, the auxiliary feature points have corresponding distribution true values;

an image processing component, configured to perform processing based on the plurality of frames of images to be processed to obtain all three-dimensional coordinate points in a same coordinate system;

a measurement processing component, configured to perform measurement processing on all the three-dimensional coordinate points to obtain target three-dimensional coordinate points; and a determination component, configured to determine a target position transformation relationship based on the target three-dimensional coordinate points and the distribution true values.

8. The apparatus for processing scanning data as claimed in claim 7, wherein the image processing component is configured to:

obtain two-dimensional coordinate points of the auxiliary feature points in each frame of image to be processed;

perform calculation based on a preset intrinsic matrix, a current-frame camera pose, and the two-dimensional coordinate points to obtain three-dimensional coordinate points of each frame of image to be processed; and register the three-dimensional coordinate points of each frame of image to be processed to obtain all the three-dimensional coordinate points.

9. An electronic device, comprising:

a processor; and a memory configured to store executable instructions of the processor, the processor being configured to read the executable instructions from the memory, and execute the instructions to implement the method for processing scanning data as claimed in claim 1.

10. A non-transitory computer-readable storage medium, wherein the non-transitory computer-readable storage medium stores a computer program, and the computer program is configured to execute the method for processing scanning data as claimed in claim 1.

11. The method for processing scanning data as claimed in claim 6, wherein the controlling the scanning device to rotate in the preset direction while scanning, at the preset frequency, the target oral cavity comprising scan posts to obtain the plurality of frames of images to be processed comprises:

controlling a monocular camera to rotate in the preset direction while scanning the target oral cavity at a specific frequency to obtain the plurality of frames of images to be processed.

12. The method for processing scanning data as claimed in claim 1, wherein the obtaining the plurality of frames of images to be processed comprising auxiliary feature points comprises:

controlling a binocular camera to cyclically scan the target oral cavity to obtain the plurality of frames of images to be processed.

13. The method for processing scanning data as claimed in claim 1, wherein the performing the measurement processing on the three-dimensional coordinate points of the auxiliary feature points to obtain the target three-dimensional coordinate points comprises:

obtaining an $N^{th}$ frame of image where three-dimensional coordinate points appear;

obtaining two-dimensional pixel coordinate points of the $N^{th}$ frame of image, and determining target three-dimensional coordinate points based on the distance between two-dimensional coordinate points projected by the three-dimensional coordinate points and the two-dimensional pixel coordinate points, where N is a positive integer.

14. The method for processing scanning data as claimed in claim 6, wherein a plurality of intraoral scan posts are installed in the target oral cavity; the intraoral scan post comprises a scan post component used for being connected with the implant, and an auxiliary component connected with the scan post component; the intraoral scan post has target features, and the target features are continuously distributed on the scan post and/or the auxiliary component, and are distributed non-unilaterally on the scan post component and/or the auxiliary component.

15. The method for processing scanning data as claimed in claim 10, wherein the method further comprises:

acquiring initial three-dimensional data of the target oral cavity based on the plurality of frames of images to be processed, and the initial three-dimensional data comprises an initial point set of the target oral cavity and three-dimensional coordinate measured values of the target features in the same coordinate system;

acquiring a preset model of the intraoral scan post, the preset model of the intraoral scan post comprises: three-dimensional coordinate true values of the target features and a real point set of the intraoral scan post in the same coordinate system, the real set comprises: three-dimensional coordinate true values of various points;

registering the initial point set of the target oral cavity and the real point set of the intraoral scan post based on a corresponding relationship between the true values and the three-dimensional coordinate measured values of the target features;

determining positioning information of the intraoral scan post is based on the registered real point set of the intraoral scan post.

16. The method for processing scanning data as claimed in claim 14, positioning information of the intraoral scan post is determined in the following manner:

during the continuous scanning process for the intraoral scan posts, the scanning data of obtaining the auxiliary feature points on the scanning post;

matching at least a portion of the scanning data with pre-stored standard reference point data, and registering the matched standard data together to obtain auxiliary feature point data in one coordinate system, wherein auxiliary feature point data of multiple scanning posts is unified in the coordinate system based on the scanning data of the scanning posts;

based on the auxiliary feature point data in the same coordinate system, determining positional information of an single intraoral scan post or the multiple intraoral scan posts; or obtaining relative positional information of the intraoral scan posts based on the positional information of each scanning post or the multiple intraoral scan posts.

* * * * *